United States Patent [19]

Kubo et al.

[11] Patent Number: 4,760,211

[45] Date of Patent: Jul. 26, 1988

[54] PROCESS FOR PRODUCING BROMINATED ACENAPHTHYLENE AND ITS CONDENSATES

[75] Inventors: Masashige Kubo; Koji Kawabata; Yukihiro Tsutsumi, all of Yamaguchi, Japan

[73] Assignee: Toyo Soda Manufacturing Co., Ltd., Shinnanyo, Japan

[21] Appl. No.: 908,799

[22] Filed: Sep. 18, 1986

[30] Foreign Application Priority Data

Sep. 27, 1985 [JP] Japan .................................. 60-212296

[51] Int. Cl.$^4$ .......................... C07C 17/00; C09K 2/10
[52] U.S. Cl. ..................................... 570/216; 570/238; 570/262; 203/67; 252/601; 252/311; 252/314
[58] Field of Search ................ 252/601, 609, 610–611, 252/311, 314; 570/206, 211, 216, 238, 262, 263; 203/67, 69

[56] References Cited

U.S. PATENT DOCUMENTS 3,586,654  6/1971  Lerman et al. ........................ 260/41
3,660,304  5/1972  Matsukawa et al. ............ 252/314 X
4,373,046  2/1983  Hagiwara et al. ................... 524/285
4,522,743  6/1985  Horn et al. ........................... 252/311

FOREIGN PATENT DOCUMENTS 128465  12/1984  European Pat. Off. .
3335400  4/1984  Fed. Rep. of Germany .
60094928  5/1985  Japan .

Primary Examiner—John F. Teraphane
Assistant Examiner—John S. Maples
Attorney, Agent, or Firm—Oblon, Fisher, Spivak, McClelland & Maier

[57] ABSTRACT

A process for recovering brominated acenaphthylene and its condensate in the form of powder, comprising dropping a solution of brominated acenaphthylene and its condensate produced from acenaphthene by reactions of bromination, condensation and dehydrobromination into hot water containing a carboxylic acid ester of polyoxyalkylene sorbitan, while the solvent is being distilled off, to recover the brominated acenaphthylene and its condensate in the form of powder dispersed in water.

7 Claims, No Drawings

PROCESS FOR PRODUCING BROMINATED ACENAPHTHYLENE AND ITS CONDENSATES

BACKGROUND OF THE INVENTION

1. Field of the Invention:

The present invention relates to a process for separating and recovering brominated acenaphthylene and its condensates in the form of powder from their solution obtained in the production course.

Brominated acenaphthylene and its condensates (designated hereinafter as Con-BACN) are compounds excellent in the uncombustive and radiation-resistive properties and, when they are admixed to various kinds of resins, they can donate to the resins the uncombustive and radiation-resistive properties. Due to the double bonds in their molecules, they can be grafted to a resin by being treated for generation of free radical. They have good immiscibility with resins because of being condensate and therefore they are noted as being capable of maintaining stable noncombustive and radiation-resistive properties for a long period of time (U.S. Pat. No. 4,373,046). Because of these properties, it is expected that Con-BACN will experience increasing use in the preparation of insulating materials for coating cables and for various resins, which materials are employed in the manufacture of parts for atomic reactors, breeder reactors and ionization radiation generators where the radiation resistance and non-combustibility properties of materials are important. The Con-BACN of this invention contains at least one bromine atom on the aromatic ring which is produced by condensation as a result of formal Friedel-Crafts' reaction of brominated acenaphthene to form polymers of the degree of condensation 2 or larger followed by the dehydrobromination reaction, including those brominated acenaphthylene produced by the dehydrobromination of brominated acenaphathene without being condensed.

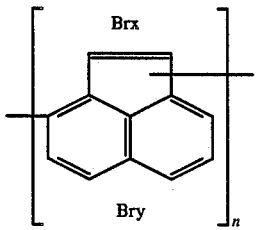

The Con-BACN of this invention is expressed by a general formula [I]; T,0030
where x is an integer 0–1, y is an integer 1–6, and n is an integer 1 or larger. The bond is formed between carbon atoms at the benzyl and the aryl positions of acenaphthylene. Thus, they are for example, 1(or 2), 5'-

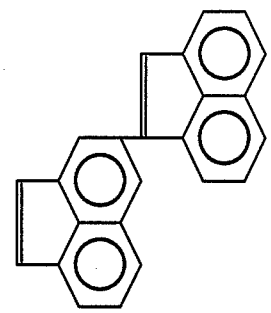

1(or 2), 6'-

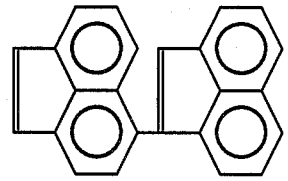

Otherwise, there may be bonds such as, for example, 1 (or 2), 3'-, 1(or 2), 4'-, 1(or 2), 7'-, and 1(or 2), 8'-. Condensates having the degree of condensation 3 or larger contain any of the bonds mentioned above to increase the number of the constitution units. The condensates referred to in the present invention are those having the degree of condensation 10 or less which are excellent in the immiscibility with resins.

Con-BACN is usually produced in powdery forms, but in resinous conglomerates when recovered by the separation method. Since the compound is intended to be used in a composition with a resin or rubber, the finely divided powdery form is favored for convenience of handling and easy dispersion when admixed to a resin composition.

2. Description of the Prior Arts:

Con-BACN is generally produced by the bromination and condensation of acenaphthene followed by the dehydrobromination reaction. Namely, bromine is added to acenaphthene in a halogenated hydrocarbon solvent in the presence of a Lewis catalyst for the bromination and condensation, and the halogenated acenaphthene condensate obtained is treated with a base such as potassium hydroxide in a methanolic solution for the dehydrobromination reaction. The dehydrobromination reaction is carried out in a solvent which is inactive to a base such as potassium hydroxide in methanol. Thus, the solvents include halogenated and aromatic hydrocarbon solvents. Therefore, the produced Con-BACN is obtained in the form of solution in a good solvent, namely halogenated or aromatic hydrocarbon. For the purpose of recovering Con-BACN in the powdery form by separation from a solution of Con-BACN, methods of reprecipitation are commonly practiced, where the solution of Con-BACN is added to a poor solvent in which Con-BACN has a slight solubility. They include, for example, a method of reprecipitation in acetone (Y. Morita and M. Hagiwara, J. Appl. Polym. Sci., 27, 3329 (1982)), a method of reprecipitation which some of the present inventors previously disclosed in U.S. patent application Ser. No. 615,541 using monohydric aliphatic alcohols containing 3 to 5 carbon atoms for the poor solvent and a method of reprecipitation disclosed in U.S. patent application Ser.

No. 615,541 which uses, as poor solvent, saturated aliphatic hydrocarbons containing 5 to 9 carbon atoms.

In these methods Con-BACN can be obtained in the form of powder, but the methods are not free from defect. Particularly, after the reprecipitation procedure, Con-BACN of low degrees of condensation remains dissolved in the filtrate, hence the recovery rate of Con-BACN is lowered. Furthermore, the condensation composition of Con-BACN is somewhat different before and after the reprecipitation and, at the same time, physical properties of the powder are accordingly varied, resulting in leaving problems in the quality control. Additional problems are recovery by separation of the good and poor solvents in the filtrate remaining after the reprecipitation and treatment of the Con-BACN dissolved in the filtrate.

For the purpose of solving these problems, some of the present inventors attempted to develop a process in which saturated aliphatic hydrocarbons were used as poor solvent to reprecipitate Con-BACN, the slurry obtained was distilled to recover the good solvent, powders of Con-BACN were separated and the filtrate was circulatingly used in the subsequent reprecipitation. This was applied for patent (U.S. patent application Ser. No. 615,541).

A good result was obtained by the separation and recovery method of the above-mentioned application, but the method was not free from troubles in operations.

In addition, troubles were also in the working environment and safe handling, because inflammable organic solvents were involved in mixing, stirring, filtering and drying. Thus, this method was not satisfactorily employed as an industrial method for separation and recovery.

SUMMARY OF THE INVENTION

While the previous processes of separating and recovering powdery Con-BACN were troublesome in operation and contained economical problems as mentioned above, the object of the present invention is to provide an economically profitable industrial process by simplifying existing processes.

A further object is to develop an industrial process in which the safety in operation is enhanced by keeping workers away from exposure to organic solvents and avoiding inflammation and explosion of inflammable organic solvents.

With the problems of previous processes in mind, the present inventors were concerned with the process in which a solution of Con-BACN is droppingly added in a heated water to disperse Con-BACN in the water in the form of powder for separation and recovery while the solvent is being removed. Through their intensive investigations they found that the strong hydrophobic property of Con-BACN prevents the Con-BACN to be obtained in the form of finely divided powders, because a viscous condensate coagulates while the solvent is being removed, and adheres to the inside wall of a tank and to blades of stirrer, to form conglomerates without forming powders of Con-BACN. Thus naturally brings about difficiulities of operation.

For dissolution of this problem, search for a dispersing agent of Con-BACN in water was made seriously. Result was that a variety of cationic, anionic and nonionic surfactants exhibit no dispersing effect when they are added in a small amount, but, if applied in a larger amount to improve the dispersion, they bubble vigorously when the solvent is stripped to such a magnitude as to prohibit satisfactory continuation of the operation.

When the amount of the dispersing agent is increased, different kinds of problems arise; disturbance of dispersing agent remaining in Con-BACN, pollution of the factory exhausts, and the cost of product increased by the necessary cost of dispersing agents. Therefore, a dispersing agent is desired which in a slight amount is capable of producing fine powders of Con-BACN.

Further search for dispersing agents revealed that among the nonionic surfactants polyoxyalkylene sorbitan carboxylic acid esters were effective in a very small amount of addition to disperse Con-BACN in water and to form finely divided particles. In addition, less bubbles were formed when the solvent was removed. Accordingly good operatability of the process accelerated the completion of the present invention. In short, the essential of this invention consists in the manufacturing process of Con-BACN comprising adding a solution of Con-BACN obtained through the production course in drops to hot water containing a polyoxyalkylene sorbitan carboxylic acid ester, while the solvent is distilled off, to recover Con-BACN in the form of powder dispersed in water.

Details of the invention will be explained below.

DETAILED DESCRIPTION OF THE INVENTION

The separation and recovery of Con-BACN of this invention can be attained by adding a solution of Con-BACN obtained in the course of production in drops to hot water containing polyoxyalkylene sorbitan carboxylic acid ester to obtain the Con-BACN in the form of powders dispersed in water while distilling of the solvent.

The organic solvents referred to in this invention which are used for Con-BACN obtained in the production course mean the good solvents to dissolve Con-BACN including those halogenated hydrocarbons and aromatic hydrocarbons which are inactive in the dehydrobromination reaction and either boil alone or azeotropically boil with water at a temperature below 100° C. They are for example carbon tetrachloride, chloroform, methylene chloride, ethylenedichloride, ethylenedibromide, chlorobenzene, benzene, toluene, xylene, and ethylbenzene.

There is no substantial restriction on the concentration of Con-BACN solution, but in usual cases a concentration of 5–70% by weight is preferred.

Polyoxyalkylene sorbitan carboxylic acid esters to be used in the present invention are obtained by converting a mixture of 1,5-sorbitan, 1,4-sorbitan, 3,6-sorbitan, 1,4,3,6-sorbide obtained by intramolecular dehydration of sorbitol into partially esterified derivatives of carboxylic acid esters, and by combining unreacting hydroxyl groups with polyoxyalkylene chains. They are expressed by general formulae [II], [III] and [IV] or a mixture thereof:

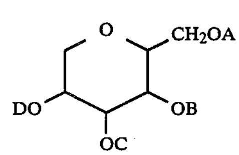

(II)

(III)

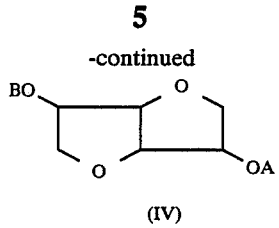

(IV)

where A is an acyl group and B, C and D are acyl groups or polyoxyalkylene groups expressed by a general formula $(C_lH_{2l}O)_mH$ (l is an integer 2–4 and m is an integer 1–50), and at least one of the substituting groups for each compound is a polyoxyalkylene group. For the carboxylic acid part of these compounds are selected those straight chain carboxylic acids which contain 10–18 carbon atoms, that is for example, lauric, palmitic, stearic and oleic acids.

Further, the HLB (hydrophilic and lipophilic balance) value of these compounds are in the range from 8 to 18.

The polyoxyalkylene sorbitan carboxylic acid esters of this invention include, for example, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate and polyoxypropylene sorbitan monolaurate. The amount of these surfactants to be applied differs somewhat depending on the working conditions. However, in most cases, it is usually 0.01 to 5 parts, preferably 0.05 to 1 part, by weight per 100 parts by weight of Con-BACN powder.

When the amount of the surfactants is less than 0.01 part by weight, the Con-BACN deposited by the removal of solvent does not disperse in good condition in the hot water, but partly coagulates not to form a uniformly dispersed powdery matter.

When the amount of the surfactants exceed 5 parts by weight, bubbles evolving at the solvent removal become somewhat vigorous which create an inferior condition of operation and the defect mentioned above.

The surfactants are usually mixed beforehand in the hot water, but it may be partially mixed into drops of the Con-BACN solution for the easy operation.

The amount of hot water in the tank where the removal of solvent takes place is determined according to the concentration of slurry of Con-BACN obtained after the solvent has been removed. The amount should be selected from the standpoint of easy handling and cost. Usually it is 0.2 to 10 liter of hot water per 100 g of Con-BACN.

The temperature of the hot water in the solvent removal tank should be higher than the boiling point of solvent of the Con-BACN solution or the temperature of the azeotropic mixture with water and it is usually 40°–100° C. approximately. While the solvent is being removed, liquid in the solvent removal tank should be thoroughly stirred so that the uniform dispersion of Con-BACN in the water results. For this purpose the solution of Con-BACN should be added to the hot water selectively either by adding in drops to the surface of water or by injecting through a nozzle of a small diameter.

The speed of dropping the Con-BACN solution in the hot water should preferably be less than the distilling speed of the organic solvent in order to prevent Con-BACN from being solidified. Specifically the speed is preferably 0.01–0.3 l/hr per liter of hot water.

The process of the present invention is usually carried out under a normal pressure, but it can be also conducted under a reduced pressure.

When the Con-BACN solution is added in drops to hot water which contains above-mentioned surfactant and the solvent is removed at the same time by the mentioned procedure, Con-BACN is separated in a short period, forming finely divided powders uniformly dispersed in the water.

The powders of Con-BACN thus deposited can be easily separated from the slurry by a conventional method, for example by centrifugation, filtration under suction and drying by spraying.

By using these methods, Con-BACN can be separated and recovered quantitatively in the form of powders from the reaction liquid obtained in the production course.

As has been clearly explained above, the process of the present invention permits the Con-BACN powders to be separated and recovered from water.

By the process of this invention, therefore, the Con-BACN powders could be quantitatively separated and recovered with more ease than that in the previous reprecipitation method employing organic solvents, hence with more ease in the production control.

Those previous problems which are concerned with recovery of Con-BACN remaining dissolved in the filtrate and the separation for recovery of solvent have been rendered unnecessary. This permits the process to be simplified to a large extent. The working environment has been much improved to a better hygienic circumstances for workers by reducing the time of exposure to organic solvents. Higher safety in operation can be obtained by not necessitating treatments of inflammable organic solvents such as stirring, mixing, filtering and drying.

The powders of Con-BACN obtained by the process of this invention have the same order of particle size as those produced by the reprecipitation method using an organic solvent. Therefore they can be easily dispersed when admixed to compositions of resins or rubber.

A Con-BACN powder prepared by the reprecipitation method with an organic solvent as precipitant often contains the organic solvent by inclusion in the particles. The solvent can be hardly removed by ordinary drying procedure. However, with the Con-BACN powders prepared by the process of this invention an organic solvent can be easily removed in an ordinary drying procedure without any additional purification process. High thermal stability is another feature of the Con-BACN powders of this invention.

In the process of the present invention, powders of Con-BACN of high quality can be separated and recovered with industrial profit in a more simplified process than previous ones.

Detailed Description of the Preferred Embodiments

The process of the present invention will be described in detail with the following embodiments, but the invention is not limited to them.

EXAMPLE 1

A mixture of 463 g of acenaphthene and 4.92 g of 2,2'-azo-bis(isobutyronitrile) was added to 1400 ml of carbon tetrachloride and the resulting solution was refluxed at 77° C. To this solution was added 312 g of bromine in solution in 460 ml of carbon tetrachloride under stirring in 0.9 hr and the reaction was continued for 0.5 hr. Then the reaction solution was cooled, 950 ml of carbon tetrachloride was added, followed by addition of 28.5 g of titanium tetrachloride at 25° C., and the reaction was continued for an additional hour. Subsequently, 8.4 g of iron powder was added to the reacting solution and 2300 g of bromine was dropwise added in 3.5 hr. The temperature was gradually elevated and the mixture was refluxed under heating for 2 hr. At the completion of the reaction, an aqueous solution of sodium hydrogen sulfite was added to remove excessive bromine and the reaction solution, after insoluble matters were removed by filtration, was thoroughly washed with water.

A solution of 336 g of potassium hydroxide in 1300 ml of methanol was added to the reaction solution, and the mixture was refluxed to react under heating for 2 hr.

Potassium bromide deposited was separated by filtration and washed with water to remove methanol, to obtain 3 l of a solution which contained 960 g of Con-BACN and 2.6 l of carbon tetrachloride.

The Con-BACN proved by analysis to contain 63.3% of bromine, and the condensation composition as estimated by high performance liquid chromatography was 18.0% of monomer, 37.6% of dimer, 27.0% of trimer and 17.4% of tetra—to octomer. Hereinafter the carbon tetrachloride solution containing Con-BACN is called 'treatment solution'. A 0.5 l aliquot of the 'reatment solution' which contains 160 g of Con-BACN was employed for the following separation and recovery.

Polyoxyethylene sorbitan monopalmitate (trade name: Leodol TW-D120, supplied from Kao Soap Co. Ltd.) in an amount of 0.48 g, having an HLB value 15.6, was dissolved in 1.5 l water and heated at 95° C. To this heated water, the above 'treatment solution' was added in drops at a speed of 0.2 l/hr under stiring, while the carbon tetrachloride was being continuously distilled off. During the distillation almost no bubbling took place and Con-BACN was immediately deposited to form fine powders which dispersed uniformly in the water. When the dropping addition of the 'treatment solution' was finished, an aqueous slurry of Con-BACN obtained was filtered, the powder was washed with 3 l of water and dried for 8 hr at 120° C. to obtain 159.7 g of reddish orange powder of Con-BACN.

Recovery of Con-BACN from the 'treatment solution' took place quantitatively. Results obtained and analysis of the Con-BACN powders are shown in Table 1.

EXAMPLE 2

In 2.5 l water, 0.4 g of polyoxyethylene sorbitan monolaurate (trade name: Tween 20 supplied from Wako Pure Chemicals Co. Ltd.) of an HLB value 16.7 was dissolved and heated to 90° C. In a 0.5 l aliquot from the 'treatment solution' prepared in Example 1 which contained 160 g of Con-BACN, 0.4 g of above-mentioned polyoxyethylene sorbitan monolaurate was dissolved and the solution obtained was dropwise added to the above heated water at a speed of 0.1 l/hr, while carbon tetrachloride was continuously being distilled. Almost no bubbling was observed during the distillation and Con-BACN deposited immediately formed fine powders and dispersed uniformly in the water.

At the completion of dropping addition of the 'treatment solution', an aqueous slurry containing Con-BACN obtained was treated in the same manner as in Example 1, to obtain fine powders of Con-BACN in reddish orange color. Results obtained and analysis of the Con-BACN powders are shown in Table 1.

EXAMPLE 3

In 2 l water, 0.36 g of polyoxyethylene sorbitan monostearate (trade name: Tween 60 supplied from Wako Pure Chemicals Co. Ltd.) of an HLB value 14.9 was dissolved and heated to 95° C. A 0.5 l aliquot from the 'treatment solution' prepared in Example 1 which contained 160 g of Con-BACN was dropwise added to the above heated stirred water at a speed of 0.2 l/hr, while carbon tetrachloride was continuously being distilled. Almost no bubbling was observed during the distillation and Con-BACN deposited immediately formed fine powders and dispersed uniformly in the water. The sequence of the procedure took place very smoothly.

At the completion of dropping addition of the 'treatment solution', an aqueous slurry containing Con-BACN obtained was treated in the same manner as in Example 1, to obtain fine powders of Con-BACN in reddish orange color. Results obtained and analysis of the Con-BACN powders are shown in Table 1.

EXAMPLE 4

In 1.5 l water, 0.48 g of polyoxyethylene sorbitan trioleate (trade name: Leodol TW-0-320 supplied from Kao Soap Co. Ltd.) of an HLB value 11.0 was dissolved and heated to 95° C. A 0.5 l aliquot from the 'treatment solution' prepared in Example 1 containing 160 g of Con-BACN, of which the solvent carbon tetrachloride was replaced by benzene so as to maintain the same solution volume, was dropwise added to the above heated stirred water at a speed of 0.2 l/hr, while the solvent benzene was continuously being distilled. Almost no bubbling was observed during the distillation and Con-BACN deposited immediately formed fine powders and dispersed uniformly in the water. The sequence of procedures took place very smoothly.

At the completion of dropping addition of the 'treatment solution', an aqueous slurry containing Con-BACN obtained was treated in the same manner as in Example 1, to obtain fine powders of Con-BACN in reddish orange color. Results obtained and analysis of the Con-BACN powders are shown in Table 1.

COMPARISON EXAMPLE 1

A 0.5 l aliquot of the 'treatment solution' in carbon tetrachloride prepared in Example 1 containing 160 g of Con-BACN was added in drops into 2 l of cold (0°—10° C.) acetone at a speed of 0.2 l/hr under stirring. At the completion of the dropwise addition, powders deposited were separated by filtration and dried at 120° C. for 8 hr, to obtain fine powders of Con-BACN in reddish orange color. Results obtained and analysis of Con-BACN powders are shown in Table 1.

COMPARISON EXAMPLE 2

A 0.5 l aliquot of the 'treatment solution' in carbon tetrachloride prepared in Example 1 containing 160 g of Con-BACN was added in drops into 2 l of i-Octane at the room temperature at a speed of 0.2 l/hr under stirring. At the completion of the dropwise addition, powders deposited were separated by filtration and dried at 120° C. for 8 hr, to obtain fine powders of Con-BACN in reddish orange color. Results and analysis of Con-BACN powders are shown in Table 1.

COMPARISON EXAMPLE 3

In 1.5 l water, 0.5 g of sodium stearate was dissolved and the solution was heated to 95° C. Into a 0.5 l aliquot from the 'treatment solution' in carbon tetrachloride prepared in Example 1 containing 160 g of Con-BACN was dropwise added to the above-mentioned heated water at a speed of 0.2 l/hr under stirring, while carbon tetrachloride was continuously being distilled. Vigorous bubbling occurred during the distillation which made the process difficult to continue and Con-BACN deposited hardly dispersed in water, but adhered mostly to the stirrer blades and the inner wall of vessel in a resinous form, so that the Con-BACN could not be obtained in the form of powder.

COMPARISON EXAMPLE 4

The same charging of materials and procedures as in Comparison Example 3 were followed, except that the surfactant was changed to stearyltrimethylammonium chloride (trade name: Cortamine 86P conc, supplied from Kao Soap Co. Ltd.). The separation and recovery of Con-BACN was not successful because of vigorous bubbling. The Con-BACN deposited adhered as resinous matters on the blades of stirrer and on the inner wall of the vessel. Powders of Con-BACN could not be obtained.

COMPARISON EXAMPLE 5

In 1.5 l water, 0.8 g of polyoxyethylene nonylphenyl ether (trade name: Nonypol 160 supplied from Sanyo Chemical Industry Ltd.) of an HLB value 15.2 was dissolved and heated to 95° C. A 0.5 l aliquot from the 'treatment solution' in carbon tetrachloride prepared in Example 1 containing 160 g of Con-BACN was dropwise added to the above-mentioned heated water at a speed of 0.1 l/hr under stirring, while the solvent carbon tetrachloride was continuously being distilled. Vigorous bubbling took place during the distillation, and the process became difficult to continue. Con-BACN deposited formed a resinous matter floating on the surface of water and therefore Con-BACN could not be obtained in the form of powder.

COMPARISON EXAMPLE 6

Separation and recovery of Con-BACN were attempted with the same charging and procedures as in Comparison Example 5, except that the surfactant was changed to sorbitan monopalmitate (trade name: Span 40 supplied from Wako Pure Chemicals Co. Ltd.) of an HLB value 6.7. Con-BACN deposited coagulated into a resinous matter without being dispersed in hot water at all. The stirrer could not be operated and the process proved impossible to conduct any further.

TABLE 1

| Result and analysis of powder | Example 1 | Example 2 | Example 3 | Example 4 | Comparison Example 1 | Comparison Example 2 |
|---|---|---|---|---|---|---|
| Result | | | | | | |
| Yield of Con-BACN (g) | 159.7 | 159.5 | 159.7 | 159.8 | 112.0 | 131.2 |
| Recovery of Con-BACN (%) | 99.8 | 99.7 | 99.8 | 99.9 | 70.0 | 82.0 |
| Mean particle diameter ($\mu$m)[1] | 8.9 | 7.6 | 8.3 | 8.7 | 9.6 | 11.3 |
| Melting point (°C.) | 144–153 | 143–153 | 144–153 | 144–153 | 152–163 | 148–160 |
| Condensation composition (HLC Ar %)[2] | | | | | | |
| Monomer | 17.9 | 18.0 | 18.0 | 17.9 | 12.7 | 14.5 |
| Dimer | 37.7 | 37.5 | 37.7 | 37.6 | 34.5 | 36.2 |
| Trimer | 27.0 | 27.1 | 27.0 | 27.1 | 29.5 | 28.3 |
| Tetramer - Octomer | 17.4 | 17.4 | 17.3 | 17.4 | 23.3 | 21.0 |
| Solvent content (% wt)[3] | | | | | | |
| Carbon tetrachloride | <0.01 | <0.01 | <0.01 | — | 1.21 | 0.77 |
| Benzene | — | — | — | <0.01 | — | — |
| Others | — | — | — | — | Acetone <0.01 | i-Octane 1.36 |
| Thermal decomposition (% wt)[4] | 0.02 | 0.03 | 0.03 | 0.02 | 0.09 | 0.10 |

Remarks
[1] The value at 50% of the particle size distribution estimated with the Coulter Counter Model TAII (manufactured by Coulter Electronics Corp.) and aperture tubes of 140 $\mu$m.
[2] Analysis made by the high performance liquid chromatography,
Apparatus: High Performance Liquid Chromatograph, Model TSK HLC 802 from Toyo Soda Manufacturing Co., Ltd.
Column: 7.5 mm diameter and 600 mm length.
Liquid: TSK GEL G1000H8 from Toyo Soda Manufacturing Co., Ltd.
[3] Analysis made by the gas chromatography.
[4] Estimated from the amount of hydrogen bromide gas evolved by heating Con-BACN powders for 3 hr at 160° C. in a nitrogen atmosphere.

What is claimed is:

1. A process for recovering brominated acenaphthylene and condensates thereof in the form of a powder, comrpising:
adding a solution of brominated acenaphthylene and condensates prepared from acenaphthene by bromination, condensation and dehyydrobromination reactions in an organic solvent dropwise to water, containing a carboxylic acid ester of polyoxyalkylene sorbitan, at a temperature higher than the boiling point of the organic solvent of said solution or higher than the temperature of an azeotrope of said solvent with water, while the solvent is being removed by distillation, to recover said brominated acenaphthylene and condensates thereof as a powder dispersed in water.

2. The process according to claim 1, wherein the organic solvent is selected from the group consisting of halogenated and aromatic hydrocarbons which can be distilled or azeotropically distilled with water at a temperature below 100° C.

3. The process according to 1, wherein the carboxylic acid ester of polyoxyalkylene sorbitan is used in an amount ranging from 0.01 to 5% by weight based on the weight of said brominated acenaphthylene and condensates thereof.

4. The process according to claim 1, wherein the carboxylic acid ester of polyoxyalkylene sorbitan is used in an amount ranging from 0.05 to 5% by weight based on the weight of said brominated acenaphthylene and condensates thereof.

5. The process according to claim 1, wherein the carboxylic acid ester of polyoxyalkylene sorbitan has an HLB value ranging from 8 to 18.

6. The process according to claim 1, wherein the carboxylic acid ester of polyoxyalkylene sorbitan is selected from the group consisting of polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate and polyoxypropylene sorbitan monolaurate.

7. The process according to claim 1, wherein the water from which said organic solvent is distilled is at a temperature ranging from about 40° to about 100° C.

* * * * *